(12) United States Patent
Aykac et al.

(10) Patent No.: US 7,164,136 B2
(45) Date of Patent: Jan. 16, 2007

(54) DETECTOR ARRAY USING A CONTINUOUS LIGHT GUIDE

(75) Inventors: Mehmet Aykac, Knoxville, TN (US); Matthias J. Schmand, Lenoir City, TN (US); Niraj K. Doshi, Knoxville, TN (US); Mark S. Andreaco, Knoxville, TN (US); Lars A. Eriksson, Oak Ridge, TN (US); Charles W. Williams, Powell, TN (US); Ronald Nutt, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 245 days.

(21) Appl. No.: 10/680,015

(22) Filed: Oct. 7, 2003

(65) Prior Publication Data

US 2005/0072904 A1   Apr. 7, 2005

(51) Int. Cl.
*G01T 3/06* (2006.01)
(52) U.S. Cl. .......................... 250/370.11; 250/390.11; 250/366
(58) Field of Classification Search ........... 250/363.03, 250/368, 367, 366, 363.02, 363.01, 370.1, 250/370.01, 208.1, 216, 239, 207, 370.11, 250/390.11
See application file for complete search history.

(56) References Cited

U.S. PATENT DOCUMENTS

| 3,919,556 | A | 11/1975 | Berninger |
| 3,936,645 | A | 2/1976 | Iverson |
| 4,749,863 | A | 6/1988 | Casey et al. |
| 4,914,301 | A | 4/1990 | Akai |
| 4,982,096 | A | 1/1991 | Fujii et al. |
| 5,059,800 | A | 10/1991 | Cueman et al. |
| 5,091,650 | A * | 2/1992 | Uchida et al. ......... 250/363.03 |
| 5,227,634 | A * | 7/1993 | Ryuo et al. ................. 250/366 |
| 5,319,204 | A | 6/1994 | Wong |
| 5,453,623 | A | 9/1995 | Wong et al. |
| 5,753,917 | A | 5/1998 | Engdahl |
| 6,087,663 | A * | 7/2000 | Moisan et al. .............. 250/367 |
| 6,292,529 | B1 | 9/2001 | Marcovici et al. |
| 6,462,341 | B1 | 10/2002 | Muehllehner |
| 6,552,348 | B1 * | 4/2003 | Cherry et al. .......... 250/363.03 |
| 2001/0040219 | A1 * | 11/2001 | Cherry et al. .......... 250/363.03 |

* cited by examiner

*Primary Examiner*—Thanh X. Luu
*Assistant Examiner*—Tony Ko

(57) ABSTRACT

A detector for use in imaging applications includes at least one detector array, an array of photodetectors, and a continuous light guide disposed between the detectors and the photodetectors. The light guide is continuous over the entire area of the photodetectors and detectors. The thickness of the light guide is optimized based on the shape of the photodetector array. Each detector array includes a plurality of scintillator elements disposed in an M×N array, where "M" and "N" are independently selectable and are each at least one. A mechanism for maintaining the relative positions of the individual scintillator elements with respect to each other is provided. The retainer is further provided to enhance the separation between the individual detector arrays to define distinct boundaries between the position profiles of the scintillator arrays.

16 Claims, 8 Drawing Sheets

DETECTOR ARRAY USING A CONTINUOUS LIGHT GUIDE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention pertains to a light guide for use in association with a detector array for use in imaging applications such as X-ray imaging, fluoroscopy, positron emission tomography (PET), single photon emission computed tomography (SPECT), computed tomography (CT), gamma camera and digital mammography systems. More particularly, the present invention pertains to a continuous light guide for use in association with a plurality of detector arrays.

2. Description of the Related Art

In the field of imaging, it is well known that imaging devices incorporate a plurality of scintillator arrays for detecting radioactivity from various sources. Each scintillator array is comprised of a plurality of scintillation crystals which interact with incident high energy photons. In Positron Emission Tomography (PET), the scintillators are provided for detecting photon energy peaks at 511 keV. At least a portion of the energy from the photons is absorbed, depending on the atomic number density (N) and effective atomic number (Z) of the scintillator. As the product (N×Z) increases, the absorption probability in the scintillator increases. Absorbed energy in the crystal is converted to lower energy scintillation photons. The scintillation photons are collected by an array of photodetectors comprised of at least one light-sensing element, such as a photomultiplier tube (PMT) or a solid state photo detector. Typical solid state photo detectors include, for example, avalanche photodiodes (APDs), PIN photodiodes and the like.

It is well known to interpose a light-transmitting media, or light guide, between the scintillator arrays and the photodetector array. The light guide is tuned using several known methods. In one such method, slots of various depths are defined in the light guide to channel the scintillation light and enhance the positioning information of the crystals. In a further such method, a reflective material such as paint is applied at various paint levels on the side surfaces of the scintillation crystals in order to channel the light to obtain uniform flood source images.

Conventional nuclear imaging systems consist of detector blocks, each of which is a modular unit in square or rectangular scintillator arrays with the dimension of M×N crystals. Alternatively, gamma cameras in nuclear imaging have a continuous scintillator, rather than pixilated, and a continuous light guide. The physical properties of the scintillator crystal play an important role on the performance of the detector system. High stopping power, short decay time and high light yield are the most desirable features for a scintillator. Crystals that have a relatively longer decay time limit the count rate capability when the imaging system is exposed to high levels of activity in the field-of-view (FOV).

It is common practice, when constructing scintillator arrays composed of discrete scintillator elements, to pack the scintillator elements together with a reflective medium interposed between the individual elements fully covering at least four sides of the scintillator element. The reflective medium serves to collimate the scintillation light to accurately assess the location at which the radiation impinges upon the detectors. The reflective medium further serves to increase the light collection efficiency from each scintillator element as well as to control the cross-talk, or light transfer, from one scintillator element to an adjacent element. Reflective mediums include reflective powders, reflective film, reflective paint, or a combination of materials.

Conventionally, scintillator arrays have been formed from polished crystals that are hand-wrapped in reflective PTFE tape and bundled together, or alternatively, glued together using a white pigment such as MgO, $BaSO_4$ or $TiO_2$ mixed with an epoxy or RTV. In a further alternative, the crystals are painted with tuned reflective paint partitions and glued with an epoxy to form the block.

Another approach utilizes individual reflector pieces that are bonded to the sides of the scintillator element with the aid of a bonding agent. This process requires iterations of bonding and cutting until a desired array size is formed.

Other devices have been produced to form an array of scintillator elements. Typical of the art are those devices disclosed in the following U.S. Patents:

| Pat. No. | Inventor(s) | Issue Date |
| --- | --- | --- |
| 3,919,556 | W. H. Berninger | Nov. 11, 1975 |
| 3,936,645 | A. H. Iverson | Feb. 3, 1976 |
| 4,749,863 | M. E. Casey et al. | Jun. 7, 1988 |
| 4,914,301 | Y. Akai | Apr. 3, 1990 |
| 4,982,096 | H. Fujii et al. | Jan. 1, 1991 |
| 5,059,800 | M. K. Cueman et al. | Oct. 22, 1991 |
| 5,319,204 | W. H. Wong | Jun. 7, 1994 |
| 5,453,623 | W. H. Wong et al. | Sep. 26, 1995 |
| 5,753,917 | J. C. Engdahl | May 19, 1998 |
| 6,087,663 | C. Moisan et al. | Jul. 11, 2000 |
| 6,292,529 | S. Marcovici et al. | Sep. 18, 2001 |
| 6,462,341 | G. Muehllehner | Oct. 8, 2002 |

Of these patents, the '645 patent issued to Iverson discloses a radiation sensitive structure having an array of cells. The cells are formed by cutting narrow slots in a sheet of luminescent material. The slots are filled with a material opaque to either light or radiation or both. The '800 patent issued to Cueman et al., discloses a similar scintillator array wherein wider slots are formed on the bottom of the array.

Wong, W. H. et al., in "An Elongated Position Sensitive Block Detector Design Using the PMT Quadrant-Sharing Configuration and Asymmetric Light Partition," *IEEE Transactions on Nuclear Science*, Vol. 46, No. 3, 542–545 (1999), discloses a block design wherein seven (7) monolithic BGO slabs are painted with light-blocking reflective patterns on their boundaries. The slabs are then glued together to form a block. The block is then cut orthogonally with respect to the glued seams and painted and glued again in like fashion. A 7×7 array is thus defined. The reflective patterns are unclear from the disclosure, but appear to be defined only for the cut portions analogous to the '863 patent discussed below, such that the reflective areas increase toward the central portion of the array.

As discussed, most of the aforementioned methods also require a separate light guide attached to the bottom of the detector array to channel and direct the light in a definitive pattern on to a receiver or set of receivers such as photomultiplier tubes or diodes. The '863 patent issued to Casey et al., discloses a two-dimensional photon position encoder system and process which includes a detector for enhancing the spatial resolution of the origin of incident photons of gamma rays. A plurality of scintillator elements interact with the incident photons and produce a quantifiable number of photons which exit the scintillation material members. A tuned light guide having a plurality of radiation barriers of predetermined lengths define slots which are operatively associated with one of the scintillator material members. The slots serve to enhance the predictability of the statistical distribution of photons along the length of the slotted light guide. A detector detects the distribution of the photons at pre-selected locations along the length of the slotted light guide.

Berninger, in the '556 patent, discloses a scintillator on which impinge incident collimated gamma rays. Light pulse output from the scintillator is detected by an array of photoelectric tubes, each having a convexly curved photocathode disposed in close proximity to the scintillator.

In the '204 (Wong) and '623 (Wong et al.) patents, a PET camera is disclosed as having an array of scintillation crystals placed next to other arrays either around or on opposing sides of a patient area. An array of light detectors is positioned next to four adjoining quadrants of four respective scintillation crystal arrays to detect radiation emitted from the four quadrants of each array. The crystals within the arrays are selectively polished and selectively bonded to adjoining crystals to present a cross-coupled interface which can tunably distribute light to adjoining light detectors. The crystal arrays are formed by optically bonding slabs of crystals into a "pre-array" and then cross-cutting the "pre-array" from one or more sides to form the final array. Wong et al. disclosed that the grooves may be optically treated, such as with white reflective fillers, for further optical control within the array.

Engdahl, in his '917 patent, discloses a scintillation camera including a scintillation crystal assembly having multiple crystal layers for interacting with various photon energy levels. The camera is disclosed as performing imaging of conventional nuclear medicine radioisotopes as well imaging of high energy isotopes used in PET applications. The multiple crystal layers have the effect of doubling the sensitivity of the camera to high energy photons, while retaining the performance characteristics needed for conventional low energy photon imaging. According to one embodiment disclosed by Engdahl, the '917 device includes a scintillation crystal having a first layer composed of NaI(T1) and a second layer composed of CsI(Na). A collimator is provided for collimating photons incident on the crystal. An array of photomultiplier tubes is provided for detecting and localizing scintillation events within the crystal. The photomultiplier tubes are mounted on a glass lightpipe.

In the '341 patent, Muehllehner discloses a positron emission detection scanner including a first plurality of detecting elements arranged in a first two-dimensional geometrical array. The detecting elements are provided for communicating light from a scintillation event. A light guide is provided for receiving light from the scintillation events from each of the detecting elements, and then transmitting the light to an array of photodetectors arranged in a second two-dimensional geometrical array, the alignment of the light sensing members being independent of the detecting elements.

Moisan et al., in the '663 patent, disclose light guides capable of encoding the transverse and longitudinal coordinates of light emission induced by the interaction of photons in an array of a plurality of the light guides. Each light guide has at least two discrete crystal segments adjacently disposed along a common longitudinal axis of the light guide. Between adjacent segments is a boundary layer having less light transmission than the light transmission of the crystal segments. A light absorbing mask is provided to increase light adsorption in a segment. Photons entering the light guide cause the emission of scintillation light which is delivered in different and resolvable quantities to light sensing devices.

Also of interest is Anger H. "Scintillation camera", Reviews of scientific instrumentation, 29(1):27–33, 1958.

BRIEF SUMMARY OF THE INVENTION

A detector for use in imaging applications such as X-ray imaging, fluoroscopy, positron emission tomography (PET), single photon emission computed tomography (SPECT), computed tomography (CT), gamma camera and digital mammography systems is provided. The detector of the present invention includes an array of detector arrays, an array of photodetectors, and a continuous light guide disposed between the detector arrays and the photodetectors. The detector arrays, as well as the photodetectors are arranged in various patterns as prescribed by the particular application. The light guide is continuous over the entire area of the photodetectors and detector arrays. The thickness of the light guide is optimized based on the shape of the photodetector array. Because the light guide is fabricated as a continuous member, having no cuts or slots, the time and expense required to fabricate the light guide is minimized.

At least one detector array is positioned on a continuous light guide, which is in turn positioned above an array of photodetectors. The photodetectors may be placed in a rectangular, hexagonal or other array as prescribed by a particular application. Each detector array includes at least one scintillator element for use in association with an imaging device. The array is fabricated such that location of the impingement of radiation upon an individual scintillator element is accurately determinable. Each array defines an M×N array of scintillator elements, where "M" and "N" are independently selectable, and where "M" is less than, equal to, or greater than "N", and where "M" and "N" are at least one. The scintillator elements define a cross-section of one or a combination of more than one geometric configuration such as circular, triangular, rectangular, hexagonal, and octagonal.

A mechanism for maintaining the relative positions of the individual scintillator elements with respect to each other is provided. The mechanism is a retainer disposed about the outermost scintillator elements to maintain the relative positions of the individual scintillator elements. The retainer is further provided to enhance the separation between the individual detector arrays to define distinct boundaries between the position profiles of the scintillator arrays. The retainer is fabricated from conventional materials such as molded plastic, shrink wrap, rubberized bands, tape or a combination of like materials may be used to enclose or hold the array together in a tight, uniform fashion. Between each of the individual scintillator elements is disposed either an air gap, a light partition, or a combination of both. The light partitions are applied or placed in the array at any selected locations between the scintillator elements in order to optimize the resultant position profile map. The height of the light partitions and the position of the light partitions within the array are selected to optimize the light transmission between the scintillator elements.

The existence or non-existence of a light partition dictates the amount of light sharing that occurs between scintillator elements. Air gaps are formed by the absence of a bonding agent between scintillator elements. The air gap between the scintillator elements, regardless of the presence of partial reflector partitions, serves to control the transmission used for early light sharing and reflection of the scintillation light within the scintillator elements. The air gap changes the total angle of reflection due to the significant index of refraction change, which results in an increase in the number of photons reflected at the crystal surface and minimizes the number of photons absorbed in the reflective material. With no light partitions, the packing fraction of the array increases to greater than 95%, and, as a result, so does the detector efficiency of the camera.

The scintillator elements are bonded to the light guide using a bonding agent. The light guide is positioned above a plurality of photodetectors. The thickness and material of the light guide is selected to optimize the light guide for the geometrical set up of the photodetectors and the light emission properties of the scintillator elements, respectively. The scintillator elements disposed within the array serve to detect an incident photon and thereafter produce a light signal corresponding to the amount of energy deposited from the initial interaction between the photon and the scintillator element. The structure of the array serves to reflect and channel the light down the scintillator element, through the light guide and to the coupled photodetector. The signal generated by the photodetector is then post-processed and utilized in accordance with the purpose of the imaging device.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

A detector for use in imaging applications such as X-ray imaging, fluoroscopy, positron emission tomography (PET), single photon emission computed tomography (SPECT), computed tomography (CT), gamma camera and digital mammography systems is provided. The detector of the present invention includes at least one detector array, an array of photodetectors, and a continuous light guide disposed between the detector arrays and the photodetectors. The detector arrays, as well as the photodetectors are arranged in various patterns as prescribed by the particular application. The light guide is continuous over the entire area of the photodetectors and detector arrays. The thickness of the light guide is optimized based on the shape of the photodetector array. Because the light guide is fabricated as a continuous member, having no cuts or slots, the time and expense required to fabricate the light guide is minimized. Illustrated the Figures are various arrangements of the detector arrays, the array of photodetectors, and the continuous light guide of the present invention.

Figure 1:
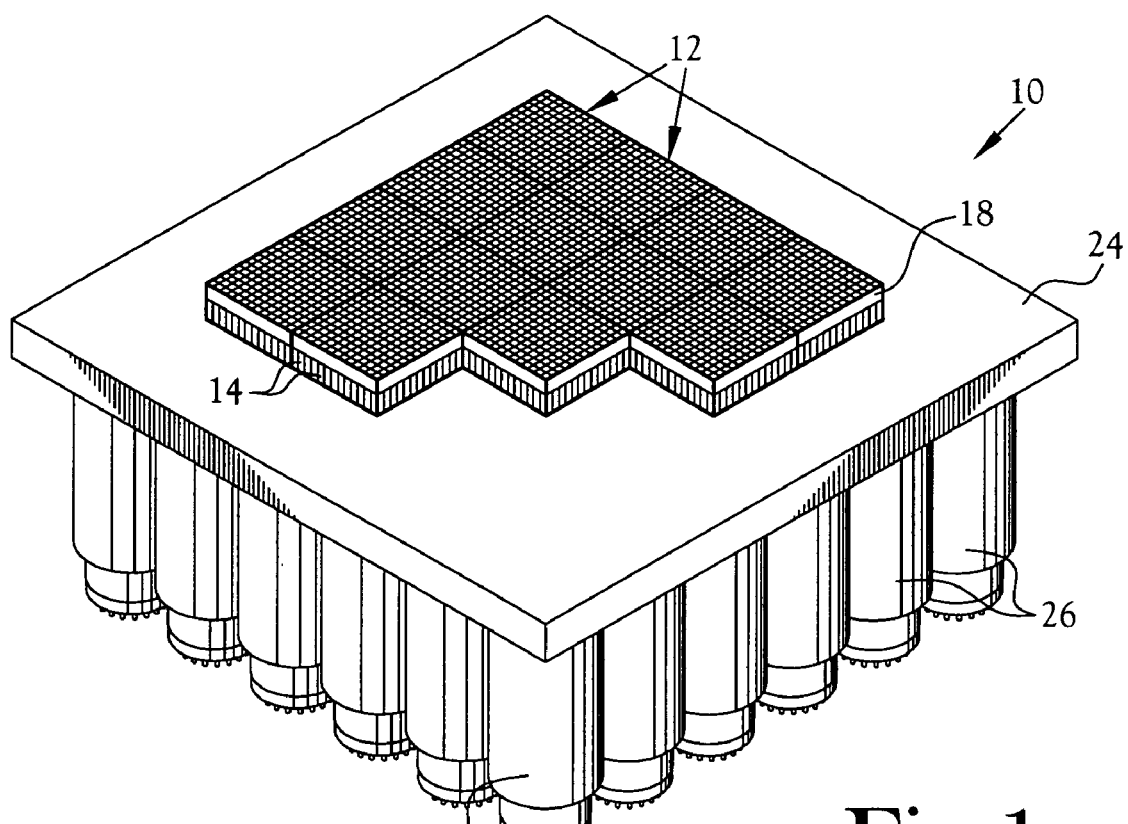
FIG. 1 is a perspective illustration of one arrangement of the detector arrays, the array of photodetectors, and the continuous light guide of the present invention.
Figure 2:
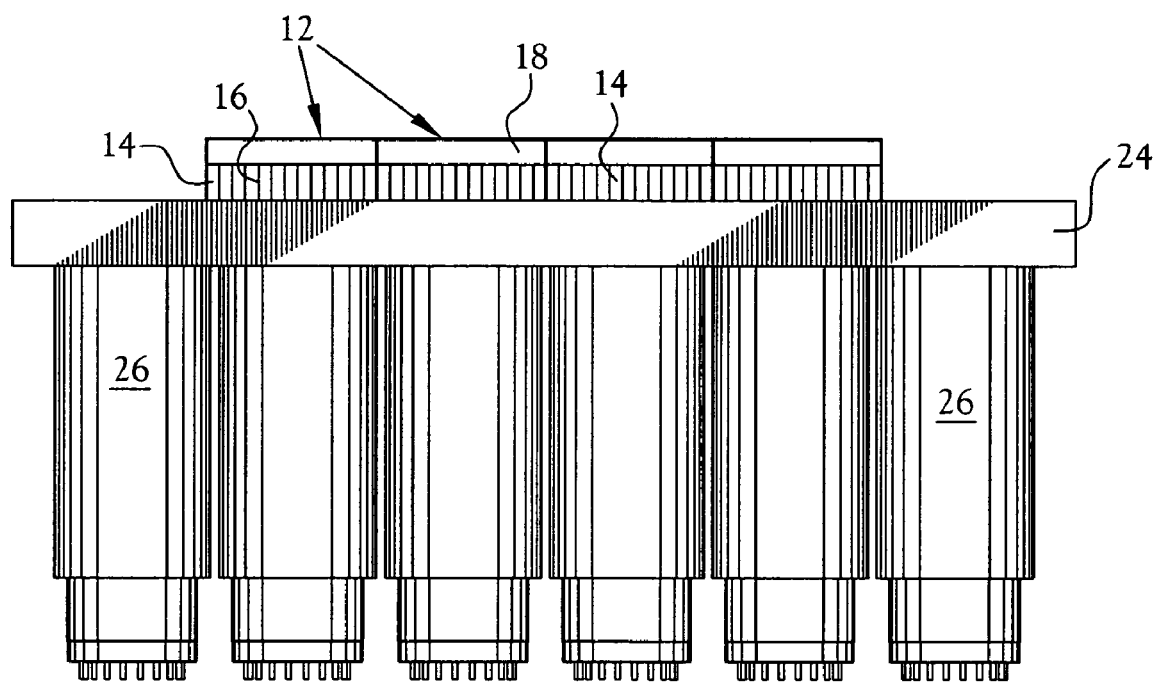
FIG. 2 is an elevation view of the arrangement of the detector arrays, the array of photodetectors, and the continuous light guide illustrated in FIG. 1.
Figure 3:
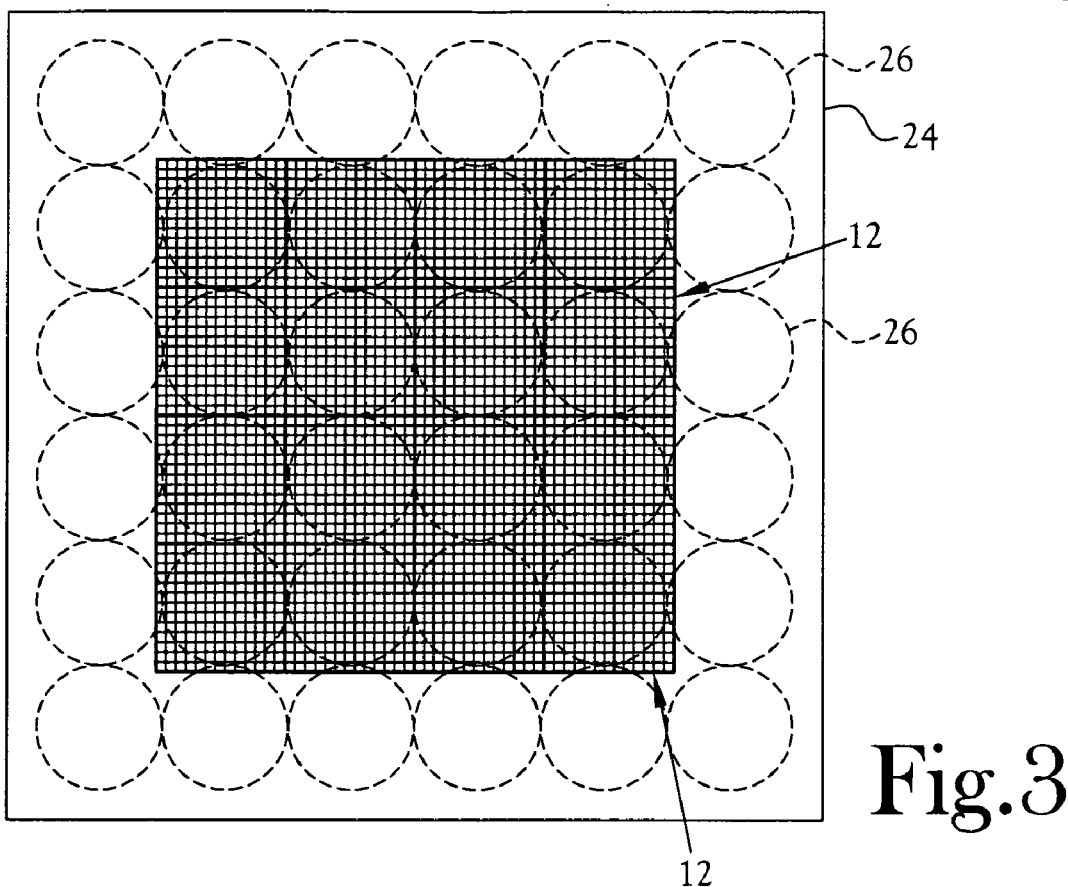
FIG. 3 is a top plan view of the arrangement of the detector arrays, the array of photodetectors, and the continuous light guide illustrated in FIG. 1, showing the relative disposition of the detector arrays with respect to the photodetectors.
Figure 4:
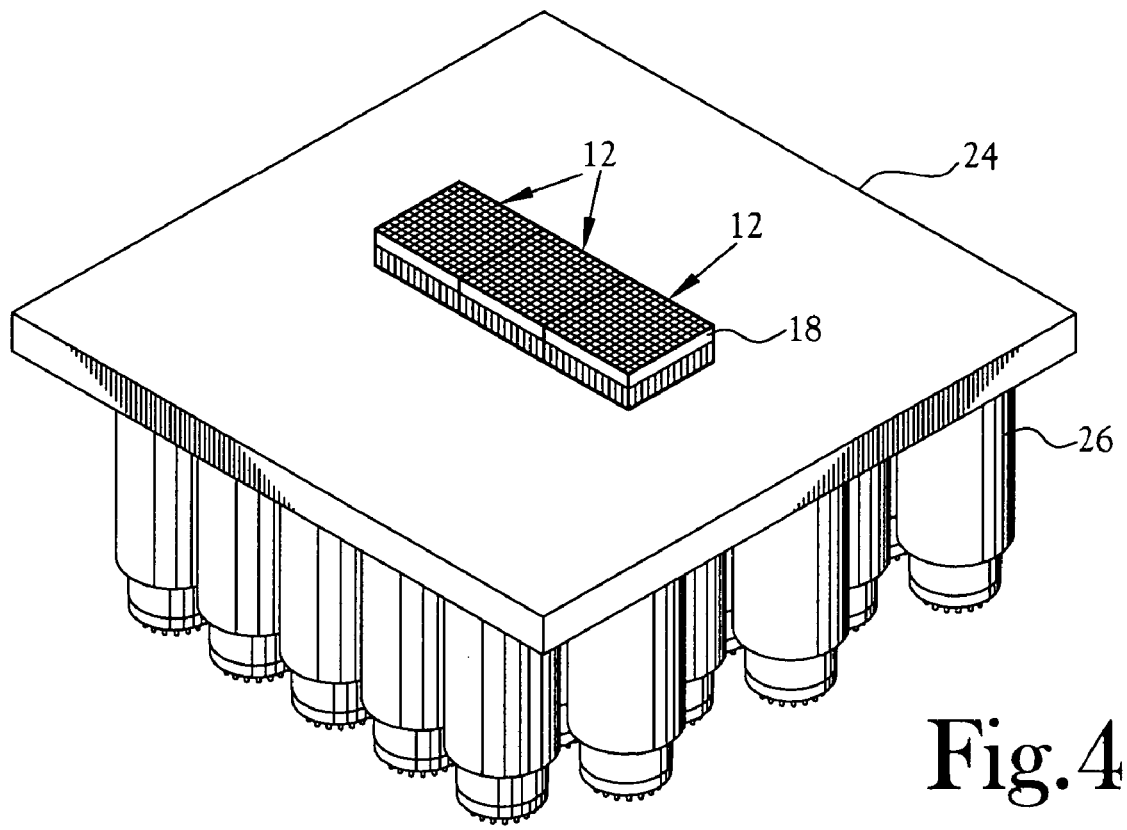
FIG. 4 is a perspective illustration of a further arrangement of the detector arrays, the array of photodetectors, and the continuous light guide of the present invention.
Figure 5:
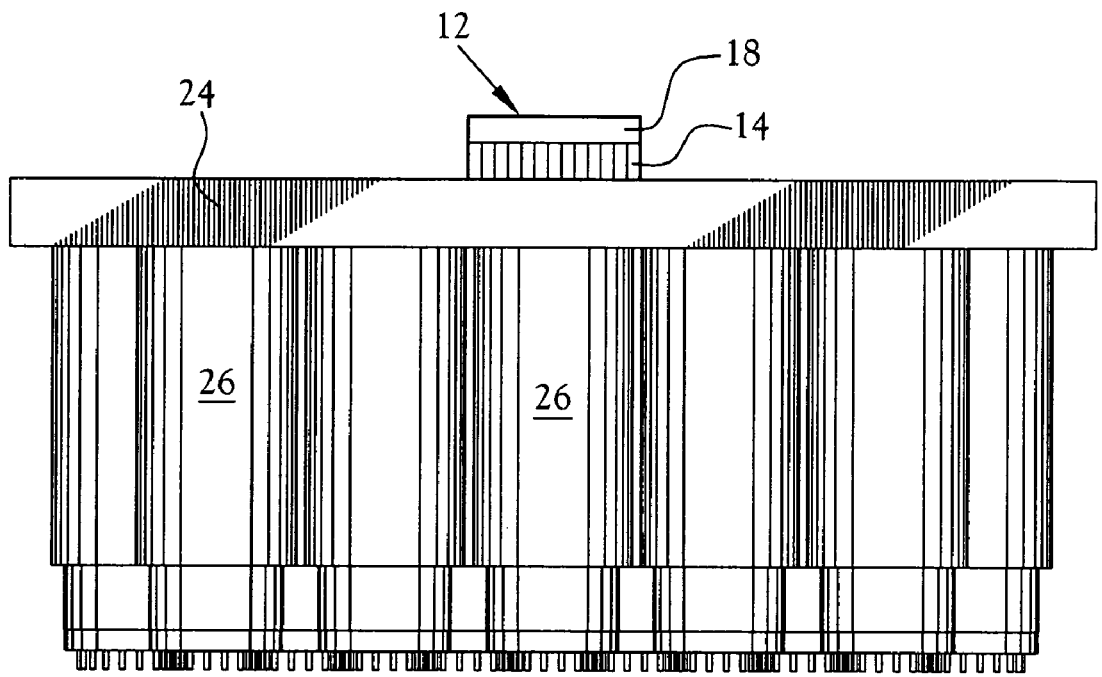
FIG. 5 is an elevation view of the arrangement of the detector arrays, the array of photodetectors, and the continuous light guide illustrated in FIG. 4.
Figure 6:
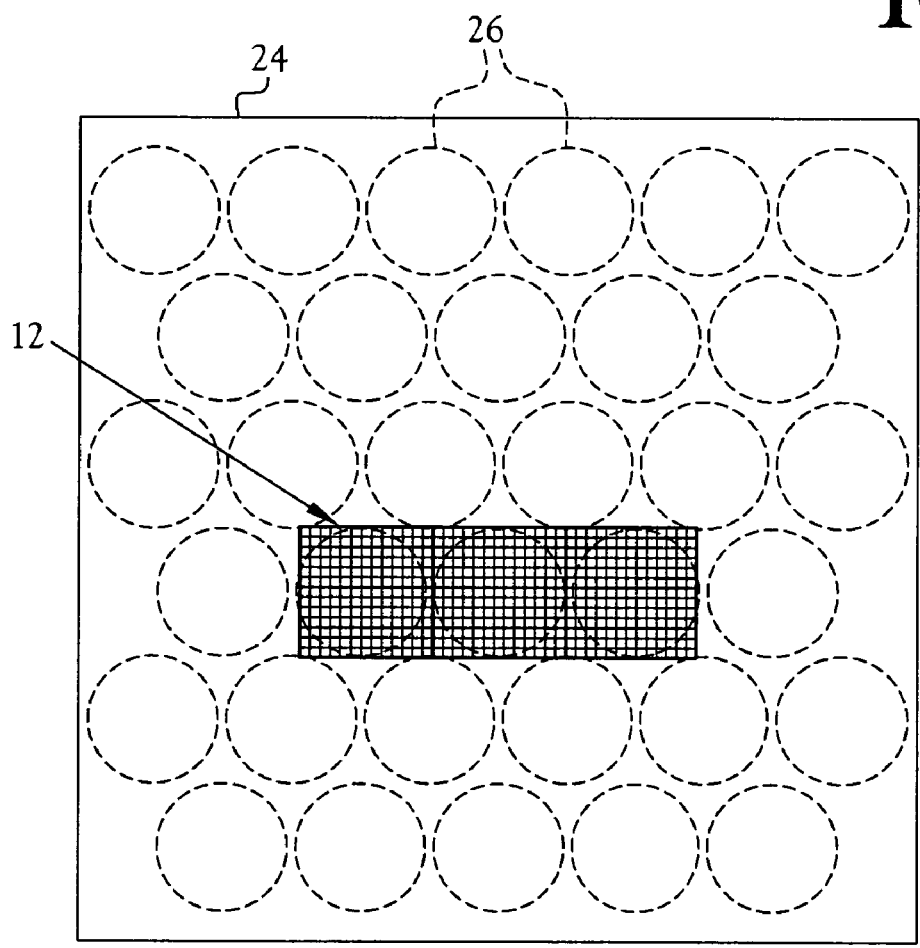
FIG. 6 is a top plan view of the arrangement of the detector arrays, the array of photodetectors, and the continuous light guide illustrated in FIG. 4, showing the relative disposition of the detector arrays with respect to the photodetectors.

FIGS. 1–3 illustrate an array of detector arrays 12 being positioned on a continuous light guide 24 which is in turn positioned above a 6×6 rectangular array of photodetectors 26. FIG. 3 most clearly illustrates the relative positions of the detector arrays 12 with respect to the photodetectors 26. Similarly, FIGS. 4–6 illustrate an array of detector arrays 12 being positioned on a continuous light guide 24 which is in turn positioned above a hexagonal array of photodetectors 26. FIG. 6 most clearly illustrates the relative positions of the detector arrays 12 with respect to the photodetectors 26.

Each detector array includes a plurality of scintillator elements 14 for use in association with an imaging device (not illustrated). The array 12 is fabricated such that location of the impingement of radiation upon an individual scintillator element 14 is accurately determinable. Each array 12 defines an M×N array of scintillator elements 14. "M" and "N" are independently selectable, with "M" being less than, equal to, or greater than "N", and "M" and "N" are at least one. The scintillator elements 14 define a cross-section of one or a combination of more than one geometric configuration such as circular, triangular, rectangular, hexagonal, and octagonal.

A mechanism 18 for maintaining the relative positions of the individual scintillator elements 14 with respect to each other is provided. In the illustrated embodiment of FIG. 1, the mechanism 18 is a retainer disposed about the outermost scintillator elements 14 to maintain the relative positions of the individual scintillator elements 14. The retainer 18 is further provided to enhance the separation between the individual detector arrays 12 to define distinct boundaries between the position profiles of the scintillator arrays 12. The retainer 18 is fabricated from conventional materials such as molded plastic, shrink wrap, rubberized bands, tape or a combination of like materials may be used to enclose or hold the array together in a tight, uniform fashion, as well as to provide reflectivity. Although illustrated as spanning only a portion of the height of the array 12, some applications may include more than one retainer 18, or may include a retainer 18 which spans the entire height of the array 12. Further, while illustrated as being disposed at the upper end of the scintillator array 12, it will be understood by those skilled in the art that the mechanism 18 may be disposed at any height along the scintillator array 12 as required.

Between each of the individual scintillator elements 14 is disposed either an air gap 16, a light partition (not illustrated), or a combination of both. The light partitions are applied or placed in the array 12 at any selected locations between the scintillator elements 14 in order to optimize the resultant position profile map. The height of the light partitions and the position of the light partitions within the array 12 are selected to optimize the light transmission between the scintillator elements 14.

In the illustrated embodiment, air gaps 16 are defined between the individual scintillator elements 14, as opposed to light partitions. The existence or non-existence of a light partition dictates the amount of light sharing that occurs between scintillator elements 14. To form an air gap 16, no bonding agent is used between scintillator elements 14. The air gap 16 between the scintillator elements 14, regardless of the presence of partial reflector partitions, serves to control the transmission used for early light sharing and reflection of the scintillation light within the scintillator elements 14. The air gap 16 changes the total angle of reflection due to the significant index of refraction change, which results in an increase in the number of photons reflected at the crystal surface and minimizes the number of photons absorbed in reflective materials used in prior art embodiments as discussed above. With no light partitions, the packing fraction of the array 12 increases to greater than 95%, and, as a result, so does the sensitivity of the camera.

In the illustrated embodiments, the detector arrays 12 are LSO scintillator arrays of 13×13 scintillator elements 14 having a pixel size of 4×4×20 mm³. The light guide 24 is an 18 mm-thick polished light guide fabricated from Lucite®. The photodetectors 26 are 2 in diameter photomultiplier tubes (PMTS) spaced approximately 2 mm apart. It will be understood that the photodetectors 26 may be spaced other than at 2 mm depending upon the particular application. The detector arrays 12 are provided with a 0.08 mm thick and 8 mm tall mechanism 18 around them. A reflector sheet such as Lumirror® may be placed on the top side of the detector arrays 12 to increase light output. Because there is no reflector between the scintillator elements 14 in the each array 12, packing fraction of the array 12 is over 99%.

In other embodiments (not illustrated), the light transmission may be optimized by providing at least a partial light partition disposed between at least a portion of the individual scintillator elements 14. For example, in one embodiment, a variable height reflective light partition is provided between selected scintillator elements 14, with the light partitions extending from the bottom surface of the array 12 and terminating toward the top surface. The height of the light partitions gradually decreases from the outermost light partitions to the center of array 12, where only air gaps 16 are provided.

Although not illustrated, the light transmission may be further optimized by varying the optical transmission properties of the scintillator surface or the reflective light partitions, such as, but not limited to, varying the thickness of the light partitions, and varying the optical density of the light partitions.

When used, the light partitions of the array 12 may be fabricated using one or more of a variety of processes utilizing materials including reflective powders, plastics, paints, polyvinyl alcohol, ceramics, films, and other highly reflective components. The light partitions are dimensioned at various lengths and thicknesses to accommodate various sized scintillator elements 14, as well as to optimize transmission properties. The array 12 is constructed to have parallel scintillator elements 14 defining either a substantially planar array 12 or an array having an arcuate configuration.

Alternatively, the light partitions may be fabricated from a reflective film such as 3M VM2000® reflective film. The film is cut to varying heights and attached to the different sides of single scintillator elements 14 based on their location in the array 12. The scintillator elements 14 are arranged in a M×N array without adhesives forming an air gap 16 between scintillator elements 14.

The scintillator elements 14 are bonded to a light guide 24 using a bonding agent 18. The light guide 24 is positioned above a plurality of photodetectors 26. The thickness and material of the light guide 24 is selected to optimize the light guide 24 for the geometrical set up of the photodetectors 26 and the light emission properties of the scintillator elements 14, respectively. The photodetector 26 is selected from, but not limited to, a photomultiplier tube, an avalanche photodiode, a pin diode, a CCD, or other solid state detector. In this arrangement, the scintillator elements 14 disposed within the array 12 serve to detect an incident photon and thereafter produce a light signal corresponding to the amount of energy deposited from the initial interaction between the photon and the scintillator element 14. The structure of the array 12 serves to reflect and channel the light down the scintillator element 14, through the light guide 24 and to the coupled photodetector 26. The signal generated by the photodetector 26 is then post-processed and utilized in accordance with the purpose of the imaging device.

Figure 7:
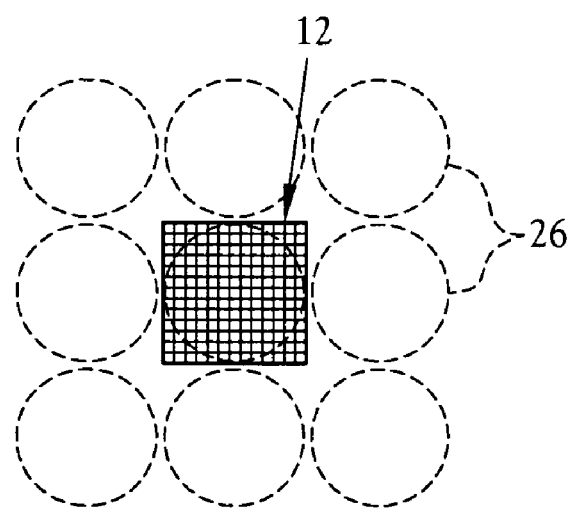
FIG. 7 is a schematic illustration of the relative disposition of a detector array with respect to an a 3×3 rectangular array of photodetectors.
Figure 8:
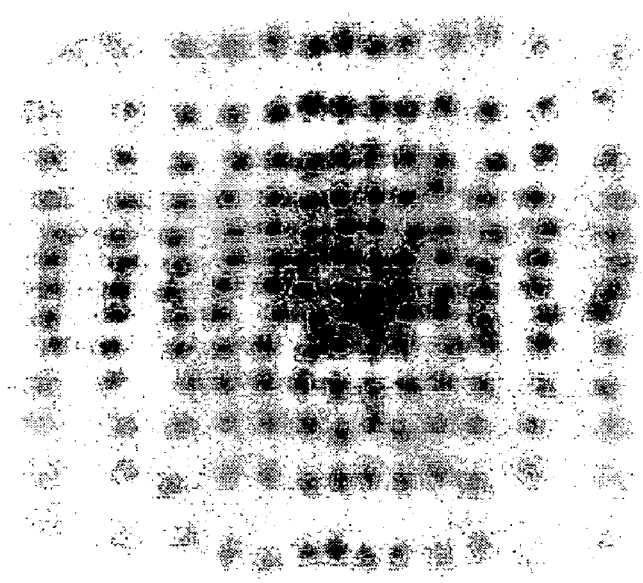
FIG. 8 is a position profile map acquired by flood irradiating the detector array of FIG. 7 with a radioactive point source.
Figure 9:
FIG. 9 is a graphical illustration of the energy peaks of each crystal in a single row of crystals of the detector array used to acquire the position profile map of FIG. 8.
Figure 10:
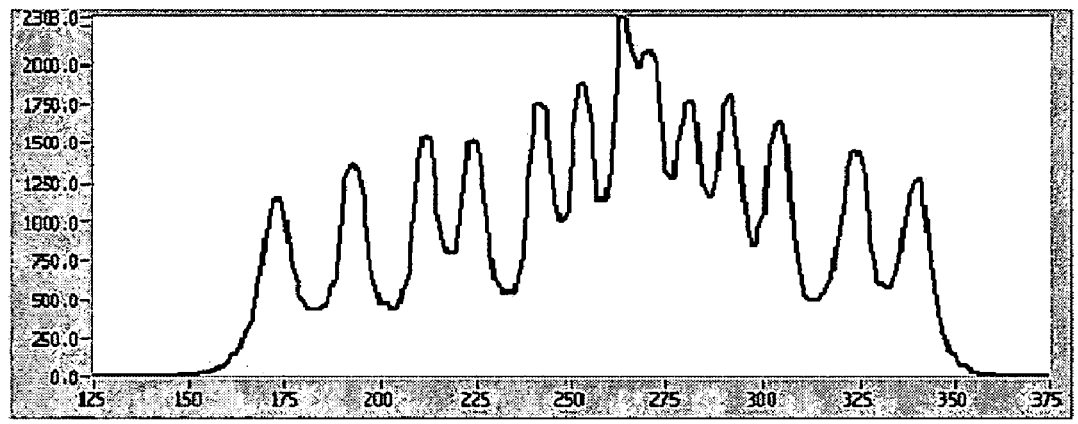
FIG. 10 is a row profile of the single row of crystals of the detector array used to acquire the position profile map of FIG. 8.

FIG. 7 illustrates the positional relationship between a detector array 12 and a 3×3 rectangular array of photodetectors 26 used for testing. The detector array 12 is comprised of a 13×13 array of scintillator elements 14. FIG. 8 illustrates a flood source image of the detector array 12 when irradiated with a radioactive point source using the array of photodetectors 26 illustrated in FIG. 7. FIG. 10 is a graphical illustration of the cross-section of the position profiles of a single row of scintillator elements 14. Energy resolution values for all of the scintillator elements 14 are measured to be 10–15% and peak-to-valley ratio (PVR) is estimated as 2.25.

Figure 11:
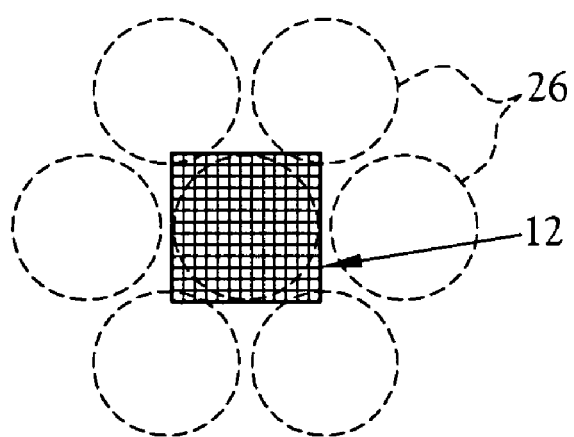
FIG. 11 is a schematic illustration of the relative disposition of a detector array with respect to a hexagonal array of seven photodetectors.
Figure 12:
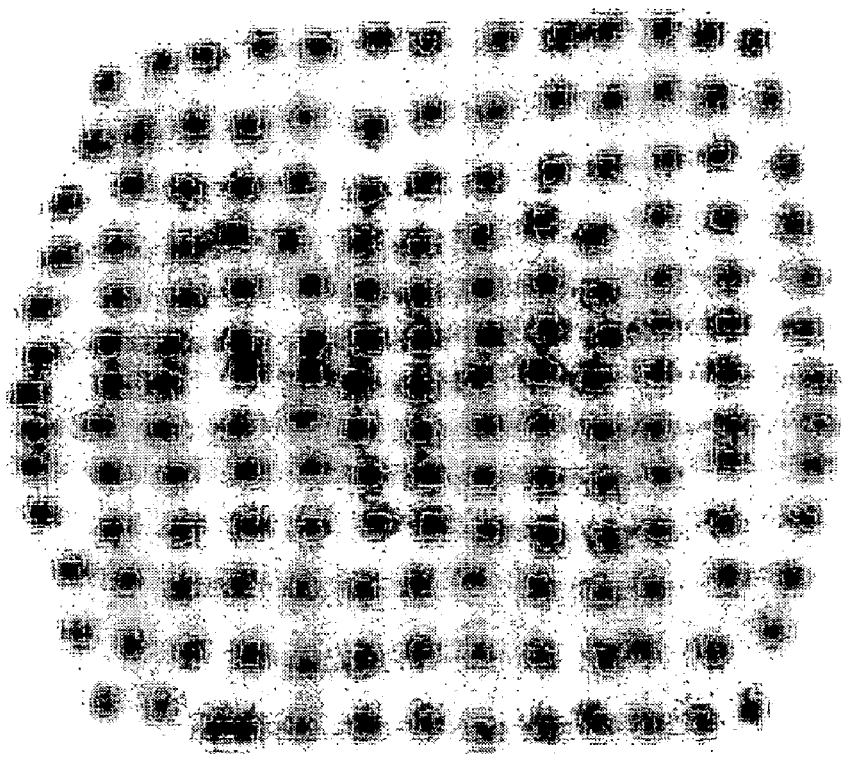
FIG. 12 is a flood source image acquired by flood irradiating the detector array of FIG. 11 with a radioactive point source.
Figure 13:
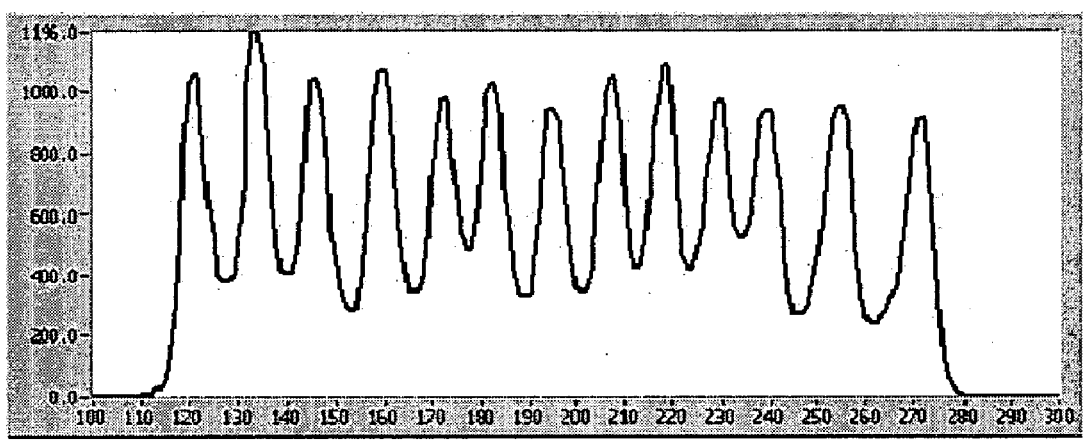
FIG. 13 is a row profile of the single row of crystals of the detector array used to acquire the position profile map of FIG. 12.
Figure 14:
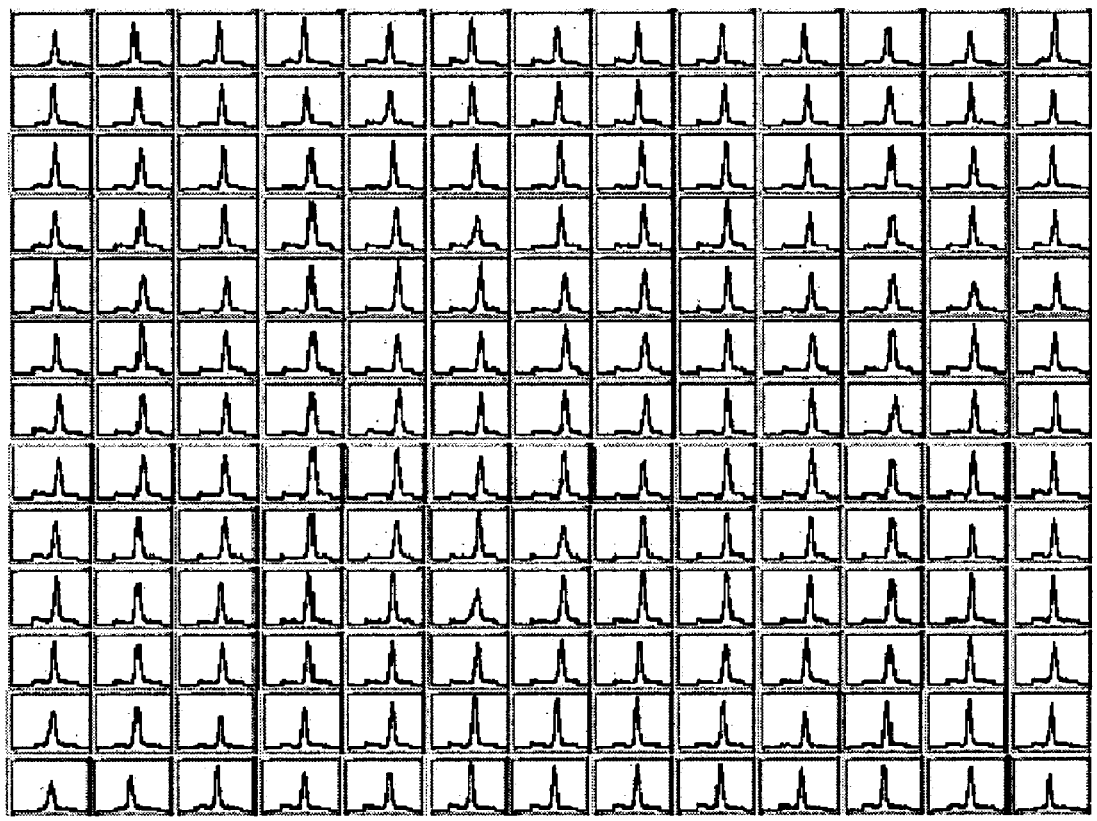
FIG. 14 is a graphical illustration of the energy peaks of each crystal of the detector array used to acquire the position profile map of FIG. 12.

FIG. 11 illustrates the positional relationship between a detector array 12 and a hexagonal array of photodetectors 26 used for testing. The detector array 12 is comprised of a 13×13 array of scintillator elements 14. FIG. 12 is a flood source image acquired by flood irradiating the detector array 12 of FIG. 11 with a radioactive point source. FIG. 13 is a profile of a single row of scintillator elements 14 of the detector array 12 used to acquire the position profile map of FIG. 12. FIG. 14 is a graphical illustration of the energy peaks of each scintillator element 14 of the detector array 12 used to acquire the position profile map of FIG. 12. The PVR in this embodiment is estimated as 3.09.

Figure 15:
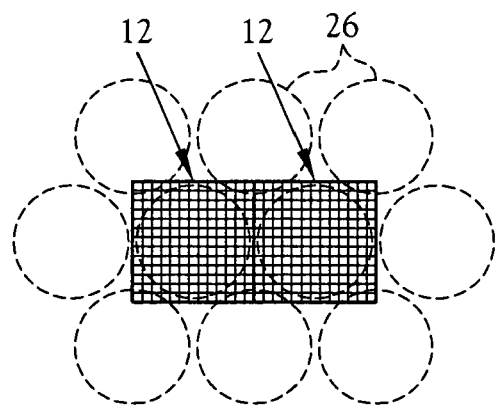
FIG. 15 is a schematic illustration of the relative disposition of two detector arrays with respect to a hexagonal array of ten photodetectors.
Figure 16:
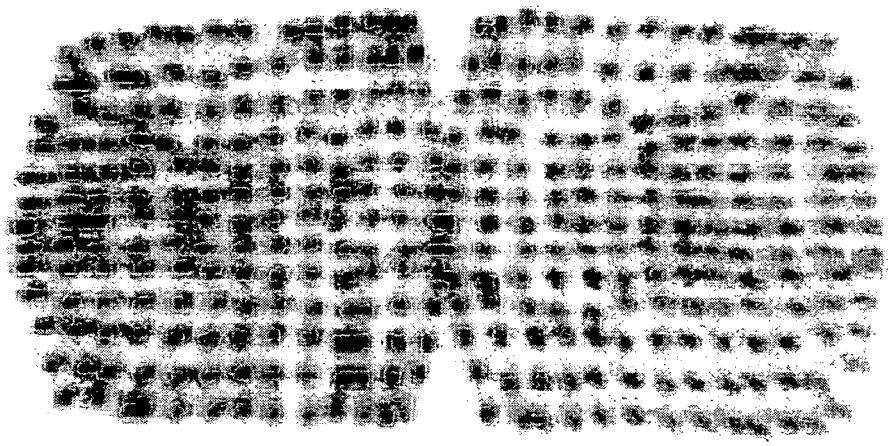
FIG. 16 is a position profile map acquired by flood irradiating the detector array of FIG. 15 with a radioactive point source, the two detector arrays having no reflectors.
Figure 17:
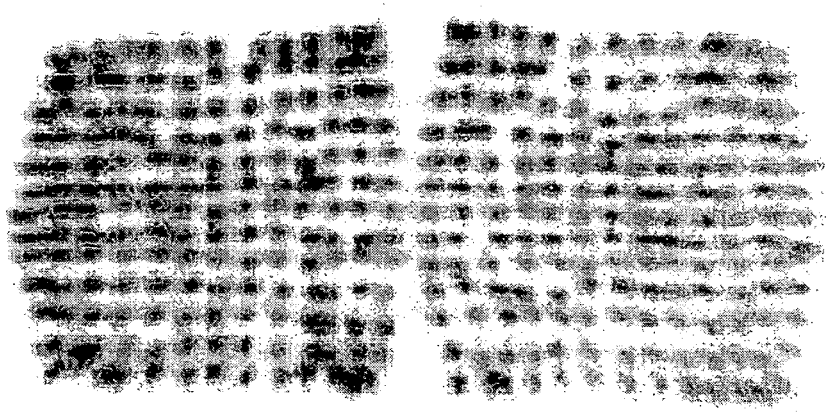
FIG. 17 is a position profile map acquired by flood irradiating the detector array of FIG. 15 with a radioactive point source, the two detector arrays having reflectors such as those illustrated in FIG. 2.

In another embodiment of the present invention, two 13×13 detector arrays 12 of scintillator crystals 14 are placed on a hexagonal PMT array as illustrated in FIG. 15. FIGS. 16 and 17 illustrate a flood source image for two cases using two detector arrays 12. In the flood source image of FIG. 16, a 2 mm air gap is defined between the two detector arrays 12. It will be understood by those skilled in the art that the detector arrays 12 may be spaced at other than a 2 mm spacing depending upon the particular application. In the flood source image of FIG. 17, a mechanism 18 defining a height of 8 mm and a thickness of 0.08 mm is disposed around each detector array 12. Each mechanism 18 is placed flush with the top side of the detector arrays 12. Separation between the detector arrays 12 is more distinct for the case in which a mechanism 18 (FIG. 17) is used. However, the average light output for a scintillator element 14 is 5% less in this case as compared to the embodiment producing the image of FIG. 16.

In a further embodiment, the output of FIG. 16 is accomplished by varying the finish on the outside faces of the scintillator crystals 14 comprising the outside surfaces of the detector arrays 12 as compared to the scintillator crystal 14 faces disposed on the interior of the detector arrays 12. By creating an optical variance between these sets of scintillator crystal 14 faces, the optical transmission from one detector array 12 to another is decreased.

From the above description, it will be recognized by those skilled in the art, that a detector for use in imaging applications such as X-ray imaging, positron emission tomography (PET), computed tomography (CT), gamma camera and digital mammography systems has been disclosed. The detector utilizes individual crystals optically coupled to a continuous light guide, the light guide having no cuts. The light guide thickness is optimized based on the shape of the photomultiplier tube array, the shape of the photomultiplier tubes and the size of the photomultiplier tubes. The present invention eliminates time required to machine the light guide to create slots or grooves, filling powder or painting.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparati and methods, and illustrative examples shown and described. Accordingly, departures may be made from such details without departing from the spirit or scope of the general inventive concept.

We claim:

1. A detector array for use in association with an imaging device, said detector array comprising:
   a plurality of M×N arrays of scintillator elements where "M" and "N" are independently selectable and where "M" and "N" are at least two;
   a mechanism for maintaining a relative position of each scintillator element in each of said plurality of M×N arrays of scintillator elements with respect to each other of said scintillator elements in each of said plurality of M×N arrays;
   a plurality of photodetectors, said plurality of M×N arrays of scintillator elements being optically coupled to said plurality of photodetectors;
   a single continuous light guide disposed between said plurality of M×N arrays of scintillator elements and said plurality of photodetectors, said continuous light guide defining no discontinuities including cuts and slots; and
   a plurality of reflective light partitions interposed between selected ones of said scintillator elements in at least one of said plurality of M×N arrays, at least one of said plurality of reflective light partitions defining a first height, and at least one of said plurality of reflective light partitions defining a second height;
   wherein said plurality of reflective light partitions is fabricated from a material selected from the group consisting of at least reflective powders, plastics, paints, polyvinyl alcohol, ceramics, and films.

2. The detector array of claim 1 wherein each of said scintillator elements defines a top surface, a bottom surface, and a plurality of side surfaces, and wherein each of said plurality of side surfaces is optimized to a selected degree to define a selected light collection efficiency and to control light sharing between said scintillator elements.

3. The detector array of claim 1 wherein an air gap is defined between adjacent selected ones of said scintillator elements in at least one of said plurality of M×N arrays.

4. The detector array of claim 3 wherein said air gap is defined between scintillator elements between which no reflective light partition is positioned.

5. The detector array of claim 1 wherein said plurality of reflective light partitions is fabricated from film, said film being adhered to one side of an adjacent pair of said selected scintillator elements, and an air gap being defined between said film and an opposing side of said adjacent pair of said selected scintillator elements.

6. The detector array of claim 1 further comprising a grid array defined by said mechanism for maintaining a relative position of each of said scintillator elements in each of said plurality of M×N arrays of scintillator elements with respect to each other of said scintillator elements and said plurality of reflective light partitions, said grid array defining a plurality of scintillator element cells adapted to receive said array of scintillator elements, said grid array being fabricated from a material selected to maximize light reflection at a wavelength particular to said scintillator elements.

7. The detector array of claim 6 wherein said at least one array of scintillator elements are received within each of said scintillator element cells without a binding agent, and an air gap being defined between each said scintillator element and a side wall of said scintillator element cell.

8. The detector array of claim 6 wherein said grid array is fabricated from at least one component selected from the group consisting of at least: reflective powders, plastics, paints, ceramics, titanium dioxide, barium sulfate, silicon dioxide, calcium carbonate, aluminum oxide, magnesium oxide, zinc oxide, zirconium oxide, talcum, alumina, Lumirror®, Teflon®, calcium fluoride, silica gel, polyvinyl alcohol, and films.

9. The detector array of claim 8 wherein said grid array is fabricated from a composition including 20% titanium dioxide ($TiO_2$), 2% Teflon®, 0.2% optical brightener, and polypropylene.

10. The detector array of claim 1 wherein said mechanism is a bonding agent for bonding scintillator elements to at least one of said photodetectors.

11. The detector array of claim 1 wherein said plurality of photodetectors is selected from the group consisting of at least a photomultiplier tube, a position sensitive photomultiplier tube, an avalanche photodiode, a pin diode, a CCD, and a solid state detector.

12. The detector array of claim 1 wherein said mechanism is a bonding agent for bonding each of said scintillator elements to said light guide.

13. A detector array for use in association with an imaging device, said detector array comprising:
    at least one M×N array of scintillator elements where "M" and "N" are independently selectable, and where "M" and "N" are at least two;
    an air gap defined between adjacent ones of said scintillator elements;
    a mechanism for maintaining a relative position of each of said scintillator elements in said at least one M×N array of scintillator elements with respect to each other of said scintillator elements;
    at least one photodetector, said array of scintillator elements being optically coupled to said at least one photodetector; and
    a continuous light guide disposed between said at least one array of scintillator elements and said at least one photodetector, said continuous light guide defining no discontinuities including cuts and slots; wherein
    said mechanism for maintaining a relative position of each of said scintillator elements in said at least one array of scintillator elements with respect to each other of said scintillator elements is a bonding agent for bonding each of said scintillator elements to said at least one photodetector.

14. The detector array of claim 13 wherein each of said scintillator elements in said at least one M×N array of scintillator elements defines a top surface, a bottom surface, and a plurality of side surfaces, and wherein each of said plurality of side surfaces is optimized to a selected degree to define a selected light collection efficiency and to control light sharing between said scintillator elements.

15. The detector array of claim 13 wherein said at least one photodetector is selected from the group consisting of at least a photomultiplier tube, a position sensitive photomultiplier tube, an avalanche photodiode, a pin diode, a CCD, and a solid state detector.

16. The detector array of claim 13 wherein said mechanism for maintaining a relative position of each of said scintillator elements of said at least one array of scintillator elements with respect to each other of said scintillator elements is a bonding agent for bonding each of said scintillator elements to said light guide.

* * * * *